United States Patent
Kim et al.

(10) Patent No.: US 7,495,022 B2
(45) Date of Patent: Feb. 24, 2009

(54) α,β-UNSATURATED HYDROXAMIC ACID DERIVATIVES AND THEIR USE AS HISTONE DEACETYLASE INHIBITORS

(75) Inventors: Dae-Kee Kim, Seoul (KR); Ju Young Lee, Suwon-shi (KR); Nam Kyu Lee, Suwon-shi (KR); Jae-Sun Kim, Suwon-shi (KR); Junwon Lee, Gunpo-shi (KR); Suk Ho Lee, Kwangmyung-shi (KR); Jin Young Choi, Suwon-shi (KR); Je Ho Ryu, Seoul (KR); Nam Ho Kim, Sungnam-shi (KR); Guang-Jin Im, Ansan-shi (KR); Tae Kon Kim, Suwon-shi (KR); Jung-Woo Seo, Seoul (KR); Young-Jue Bang, Seoul (KR)

(73) Assignee: SK Chemicals Co., Ltd., Suwon-Si (KR)

( * ) Notice: Subject to any disclaimer, the term of this patent is extended or adjusted under 35 U.S.C. 154(b) by 594 days.

(21) Appl. No.: 10/510,630

(22) PCT Filed: Apr. 10, 2003

(86) PCT No.: PCT/KR03/00721

§ 371 (c)(1), (2), (4) Date: Oct. 8, 2004

(87) PCT Pub. No.: WO03/087066

PCT Pub. Date: Oct. 23, 2003

(65) Prior Publication Data

US 2005/0124679 A1    Jun. 9, 2005

(30) Foreign Application Priority Data

Apr. 11, 2002    (KR) .................... 10-2002-0019712

(51) Int. Cl.
  *A61K 31/19*    (2006.01)
  *C07D 207/32*    (2006.01)
(52) U.S. Cl. .................. 514/408; 514/575; 548/561; 562/621
(58) Field of Classification Search ............ 514/408, 514/575; 548/561; 562/621
  See application file for complete search history.

(56) References Cited

FOREIGN PATENT DOCUMENTS

| WO | WO 01/38322 A1 | 5/2001 |
| WO | WO 02/22577 | 3/2002 |

*Primary Examiner*—Kamal A Saeed
(74) *Attorney, Agent, or Firm*—Finnegan, Henderson, Farabow, Garrett & Dunner, L.L.P.

(57) ABSTRACT

Disclosed are agents that inhibit histone deacetylase. More specifically, the present invention relates to novel hydroxamic acid derivatives or pharmaceutically acceptable salts thereof for anticancer agents or other therapeutic agents based on their histone deacetylase inhibitory activity.

4 Claims, 1 Drawing Sheet

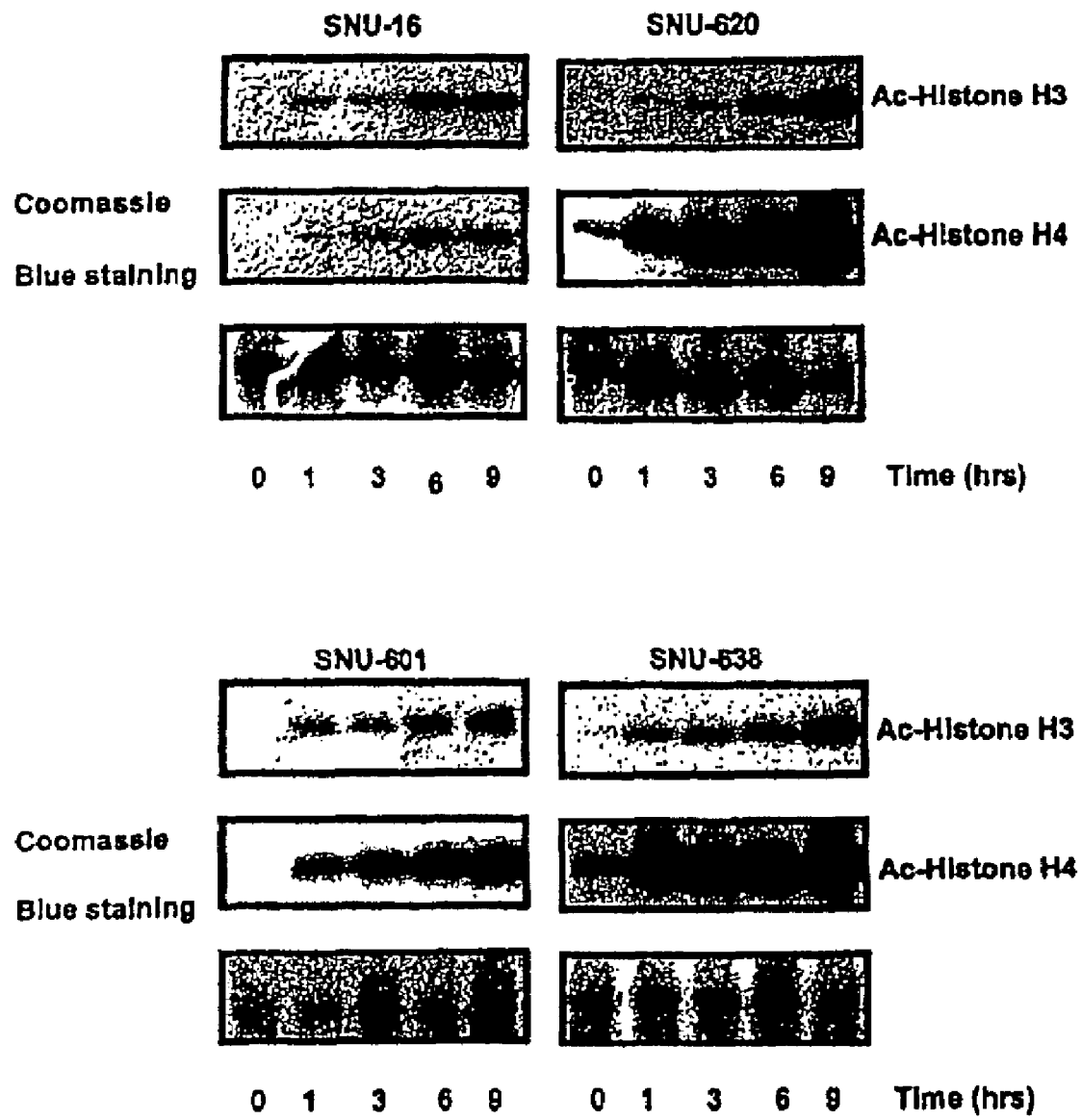

α,β-UNSATURATED HYDROXAMIC ACID DERIVATIVES AND THEIR USE AS HISTONE DEACETYLASE INHIBITORS

BACKGROUND OF THE INVENTION

1. Field of the Invention

This invention relates to histone deacetylase inhibiting agents. In particular, the present invention relates to novel hydroxamic acid derivatives or pharmaceutically acceptable salts thereof for anticancer agents or other therapeutic agents based on their histone deacetylase inhibitory activity.

2. Description of the Art

Cancer is one of the most common cause of death in the developed world. Despite advances in the diagnosis and management of many cancers, only minor improvements in cure and survival rates have been realized. The incidence of cancer is rising as a result of ageing populations and complex environmental and lifestyle factors. Cancer imposes great costs on society and individuals via premature disability, mortality and high treatment costs. To date many anticancer drugs have been investigated, but no satisfactory drugs have been discovered. So an anticancer drug with reduced toxicity and high therapeutic effect has been desired.

Key nuclear processes such as DNA replication, transcription, repair, and rearrangements during differentiation are influenced by chromatin structure and the binding of regulatory proteins to DNA. These processes can be modulated by the acetylation level of nucleosomal histones. Histone deacetylases and the family of histone acetyltransferases are involved in determining this acetylation of histones, which play a role in regulation of gene expression. Increasing evidence indicates that cellular proteins involved in the regulation of proliferation and differentiation exert their function by recruitment of histone acetyltransferases or deacetylases. In various cases aberrant histone acetylation has been linked to malignant disease.

A number of histone deacetylase inhibitors have been identified that induce cultured tumor cells to undergo growth arrest, differentiation, and/or apoptotic cell death. Several of these agents, the hydroxamic acid based histone deacetylase inhibitors in particular, inhibit tumor growth in animals at doses that cause little or no toxicity [Paul A. Marks et al., Current Opinion in Oncology, 2001, 13, 477-483].

SUMMARY OF THE INVENTION

An objective of this invention is to provide a compound which has a histone deacetylase inhibitory activity and is useful as a therapeutic or improving agent for malignant tumors. We have attempted to achieve the above objective and have found that novel α,β-unsaturated hydroxamic acid derivatives having histone deacetylase inhibitory activity show promising antitumor effect.

This invention provides compounds represented by formula (1) or pharmaceutically acceptable salts thereof

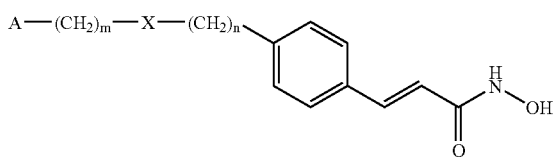

wherein A is an optionally substituted phenyl or aromatic heterocyclic group which has 1 to 4 substituents selected from the group consisting of a halogen atom, a hydroxyl group, an amino group, a nitro group, a cyano group, an alkyl group having 1 to 4 carbons, an alkoxy group having 1 to 4 carbons, an aminoalkyl group having 1 to 4 carbons, an alkylamino group having 1 to 4 carbons, an acyl group having 1 to 4 carbons, an acylamino group having 1 to 4 carbons, an alkylthio group having 1 to 4 carbons, a perfluoroalkyl group having 1 to 4 carbons, a perfluoroalkoxy group having 1 to 4 carbons, a carboxyl group, an alkoxycarbonyl group having 1 to 4 carbons, a phenyl group, an aromatic heterocyclic group and a heterocyclic group, said heterocyclic group being optionally substituted with an alkyl group having 1 to 4 carbons, a benzyl group, or a pyridylmethyl group;

m is an integer of 0 to 4;

n is an integer of 1 to 4;

X is a moiety having a structure selected from those illustrated in formula (2)

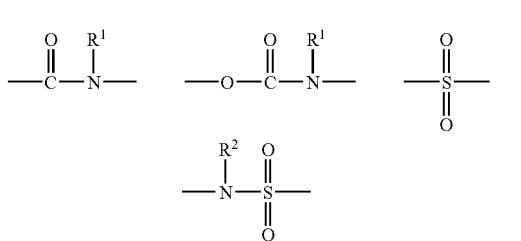

$R^1$ and $R^2$ are independently H or an optionally substituted alkyl group having 1 to 4 carbons

BRIEF DESCRIPTION OF THE DRAWINGS

The sole FIGURE shows in vitro inhibition of histone deacetylase in accordance with Example 5.

DETAILED DESCRIPTION OF THE INVENTION

Throughout this specification, the term aromatic heterocyclic group means a 5-6 membered aromatic ring containing one or more atoms selected from oxygen, sulfur and nitrogen atoms on the ring, said ring being optionally condensed with a carbon ring or other heterocyclic ring.

Examples include pyrrole, indole, carbazole, imidazole, pyrazole, benzimidazole, pyridine, naphthyridine, furopyridine, thienopyridine, pyrrolopyridine, oxazolopyridine, imidazolopyridine, thiazolopyridine, quinoline, isoquinoline, acridine, phenanthridine, pyridazine, pyrimidine, pyrazine, cinnoline, phthaladine, quinazoline, naphthylidine, quinoxaline, isoxazole, benzisoxazole, oxazole, benzoxazole, benzoxadiazole, isothiazole, benzisothiazole, thiazole, benzthiazole, benzthiadiazole, furan, benzofuran, thiophen, benzothiophen, and the like.

The term heterocyclic group means a 5-6 membered ring containing one or more atoms selected from oxygen, sulfur and nitrogen atoms on the ring, said ring being optionally condensed with a carbon ring or other heterocyclic ring.

Examples include pyrrolidine, piperidine, piperazine, morpholine, thiomorpholine and the like.

As used herein, "1 to 4 carbons" means a carbon number per a single substituent; for example, for dialkyl substitution it means 2 to 8 carbons.

A halogen may be fluorine, chlorine, bromine or iodine.

An alkyl having 1 to 4 carbons includes methyl, ethyl, n-propyl, isopropyl, n-butyl, isobutyl, sec-butyl and tert-butyl.

An alkoxy having 1 to 4 carbons includes methoxy, ethoxy, n-propoxy, isopropoxy, allyloxy, n-butoxy, isobutoxy, sec-butoxy, tert-butoxy and the like.

An alkylamino having 1 to 4 carbons includes N-methylamino, N,N-dimethylamino, N,N-diethylamino, N-methyl-N-ethylamino, N,N-diisopropylamino and the like.

An acyl having 1 to 4 carbons includes acetyl, propanoyl, butanoyl and the like.

An acylamino having 1 to 4 carbons includes acetylamino, propanoylamino, butanoylamino and the like.

An alkylthio having 1 to 4 carbons includes methylthio, ethylthio, n-propylthio and the like.

A perfluoroalkyl having 1 to 4 carbons includes trifluoromethyl, pentafluoroethyl and the like.

A perfluoroalkoxy having 1 to 4 carbons includes trifluoromethoxy, pentafluoroethoxy and the like.

An alkoxycarbonyl having 1 to 4 carbons includes methoxycarbonyl, ethoxycarbonyl and the like.

An optionally substituted alkyl having 1 to 4 carbons includes methyl, ethyl, n-propyl, isopropyl, n-butyl, isobutyl, sec-butyl and tert-butyl and these having 1 to 4 substituents selected from the group consisting of a halogen, hydroxy, amino, nitro, cyano, phenyl and a heterocycle.

Compounds of the general formula (1) may be prepared from compounds of the general formula (3):

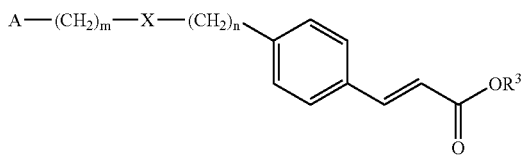

3 wherein A, m, X, and n are as defined above; $R^3$ is H or an alkyl group having 1 to 4 carbons. The reaction (when $R^3$ is an alkyl group having 1 to 4 carbons) is generally carried out at from 0° C. to room temperature for 1-24 hours in a suitable solvent such as a $C_1$-$C_3$ alkanol, dichloromethane, or N,N-dimethylformamide (DMF), using an excess amount of hydroxyamine salt in the presence of a base such as sodium hydroxide, potassium hydroxide, sodium carbonate, potassium carbonate, or potassium tert-butoxide. The reaction (when $R^3$ is H) may be also carried out with a carboxylic acid activator to give a reactive derivative and allowed to react with an excess amount of hydroxyamine salt under anhydrous conditions at from 0° C. to room temperature for 1-24 hours in a suitable solvent such as tetrahydrofuran (THF), acetone, dichloromethane, or DMF, in the presence of a base such as triethylamine, pyridine, sodium hydroxide, potassium hydroxide, sodium carbonate, or potassium carbonate. The carboxylic acid activators include thionyl chloride, phosphorous pentachloride, phosphorous oxychloride, oxalyl chloride and the like.

Compounds of the general formula (3) may be prepared from compounds of the general formula (4) and (5):

4

-continued

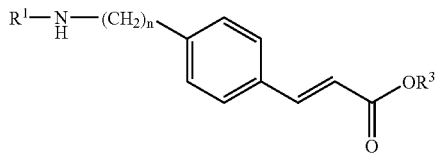

5 wherein A, m, $R^1$, n, and $R^3$ are as defined above; $R^4$ is OH or $CO_2H$. The coupling reaction (when $R^4$ is OH) is generally effected by using a well-known reagent in the literature, preferably 1,1-carbonyldiimidazole (CDI) or triphosgen, in the presence of an organic tertiary amine such as triethylamine, optionally in the presence of a catalyst such as 4-dimethylaminopyridine (DMAP), in an inert solvent such as THF, acetonitrile, dichloromethane or DMF, at from 0° C. to room temperature for 2-24 hours. The coupling reaction (when $R^4$ is $CO_2H$) is generally effected by using an excess amount of a well-known reagent in the literature, preferably 1,3-dicyclohexylcarbodiimide (DCC), bis(2-oxo-3-oxazolidinyl) phosphinic chloride (BOP-Cl) or 1-(3-dimethylaminopropyl)-3-ethylcarbodiimide hydrochloride (EDC), in the presence of an excess of 1-hydroxybenzotriazole, optionally in the presence of a catalyst such as DMAP, in an inert solvent such as dichloromethane or DMF, at from 0° C. to room temperature for 2-24 hours. For convenience, pyridine may also be used as a solvent. The reaction may be also carried out using a carboxylic acid activator as defined above.

Compounds of the general formula (3) may be also prepared from compounds of the general formula (6):

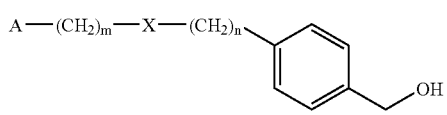

6 wherein A, m, X, and n are as defined above. The reaction is generally carried out by first converting a compound of the formula (6) to the corresponding aldehyde using well-known methods in the literature, preferably Swern oxidation, and then the aldehyde is subjected to the Wittig reaction.

Compounds of the general formula (6) may be prepared from compounds of the general formulas (7) and (8):

7

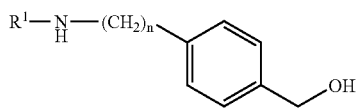

8 wherein A, m, $R^1$, $R^4$, and n are as defined above. The reaction is generally carried out under the same conditions as in the coupling reaction above.

Compounds of the general formula (6) may be also prepared from compounds of the general formula (9):

$$A-(CH_2)_m-X-(CH_2)_n-\underset{O}{\underset{\|}{C}}-\text{C}_6H_4-OR^5 \quad (9)$$

wherein A, m, X, and n are as defined above; $R^5$ is an alkyl group having 1 to 4 carbons. The reduction reaction is generally carried out under an anhydrous condition using a well-known reducing agent in the literature, preferably $LiAlH_4$ or diisobutylaluminum hydride (DIBAL-H), at from 0° C. to reflux temperature for 1-24 hours.

Compounds of the general formula (9) may be prepared from compounds of the general formulas (10) and (11):

$$A-(CH_2)_m-\underset{H}{N}-R^2 \quad (10)$$

$$ClSO_2-(CH_2)_n-\text{C}_6H_4-\underset{O}{\underset{\|}{C}}-OR^5 \quad (11)$$

wherein A, m, $R^2$, n and $R^5$ are as defined above. The coupling reaction is generally carried out at from 0° C. to room temperature for 1-24 hours in a suitable solvent such as a $C_1$-$C_4$ alkanol, dichloromethane, DMF, or water using an excess amount of (10) or in the presence of an organic tertiary amine such as triethylamine or an inorganic base such as potassium carbonate, to scavenge the acid by-product.

Compounds of the general formula (9) may be also prepared from compounds of $$A-(CH_2)_m-S-(CH_2)_n-\text{C}_6H_4-\underset{O}{\underset{\|}{C}}-OR^5 \quad (12)$$

the general formula (12):

wherein A, m, n and $R^5$ are as defined above. The oxidation reaction is generally effected by using an excess amount of a well-known reagent in the literature, preferably OXONE, in a solvent such as aqueous $C_1$-$C_4$ alkanol, at from 0° C. to room temperature for 2-24 hours.

Compounds of the general formula (12) may be prepared from compounds of the general formulas (13) and (14):

$$A-(CH_2)_m-SH \quad (13)$$

$$R^8-(CH_2)_n-\text{C}_6H_4-\underset{O}{\underset{\|}{C}}-OR^5 \quad (14)$$

wherein A, m, n and $R^5$ are as defined above; $R^6$ represents a halogen atom, preferably a chlorine atom. The alkylation reaction is generally carried out under standard conditions in the presence of a base such as potassium carbonate or potassium tert-butoxide, in a suitable solvent such as DMF, at room temperature to 100° C. for 2-24 hours.

Compounds represented by formula (1) may be purified or isolated by a usual separation method such as extraction, recrystallization, column chromatography and the like.

Compounds of this invention can be orally or parenterally administered. In case of oral administration, compounds of this invention may be formulated into solid formulations such as tablets, powders, granules, capsules and the like; solutions; oily suspensions; or liquid formulations such as syrups, elixirs and the like. In case of parenteral administration, compounds of this invention may be formulated into aqueous or oily suspension for injection. In preparing the formulations, conventional excipients, binders, lubricants, aqueous solvents, oily solvents, emulsifiers, suspending agents or the like may be used, and other additives, such as preservatives, stabilizers or the like may be also included.

Although appropriate daily dosages of the compounds of this invention vary depending upon the administration route, age, body weight and conditions of the patient, and the kind of disease to be treated, they can generally be between 0.05-1000 mg, preferably 10-1000 mg on oral administration, and 0.01-300 mg, preferably 0.05-100 mg on parenteral administration, in 1-5 divisions.

The following Examples are provided to further illustrate this invention and are not to be constructed as limiting thereof.

EXAMPLES

Example 1

N-[4-(2-Hydroxycarbamoylvinyl)benzyl]-4-(4-pyridin-3-ylmethylpiperazin-1-yl)benzamide (1-1) 4-(4-Pyridin-3-ylmethylpiperazin-1-yl)benzonitrile A suspension of 1-(pyridin-3-ylmethyl)piperazine (549 mg, 3.10 mmol), 4-fluorobenzonitrile (375 mg, 3.10 mmol), and $K_2CO_3$ (643 mg, 4.65 mmol) in DMF (50 mL) was stirred at 80° C. overnight. The reaction mixture was cooled to room temperature and filtered, and the filtrate was washed with ethyl acetate (30 nL). The combined filtrate and washings were evaporated to dryness under reduced pressure. The crude residue was purified by MPLC on silica gel (3% MeOH in $CH_2Cl_2$) to afford the titled compound (326 mg, 38%) as a yellow solid.

$^1$H NMR (CDCl$_3$/TMS) δ 2.59 (apparent t, 4H, J=5.1 Hz), 3.33 (apparent t, 4H, J=5.1 Hz), 3.57 (s, 2H), 6.85 (m, 2H), 7.27 (m, 1H), 7.48 (m, 2H), 7.69 (m, 1H), 8.53 (m, 1H), 8.57 (m, 1H)

(1-2) 3-(4-{[4-(4-Pyridin-3-ylmethylpiperazin-1-yl)benzoylamino]methyl}phenyl)acrylic acid ethyl ester A solution of the compound (330 mg, 1.19 mmol) from the process (1-1) in conc. HCl (20 mL) was stirred at 80° C. overnight. The reaction mixture was cooled to room temperature and then evaporated to dryness under reduced pressure. The residue was dissolved in saturated LiOH solution (pH 9) and then evaporated to dryness under reduced pressure. The residue was dissolved in 10% aqueous HCl solution (pH 2), evaporated, and dried under vacuum to give the corresponding acid, which was used in the next step without further purification.

To a mixture of the acid above, 3-(4-aminomethylphenyl) acrylic acid ethyl ester hydrochloride (287 mg, 1.19 mmol), 1-hydroxybenzotriazole (240 mg, 1.78 mmol), and DMAP (29 mg, 0.24 mmol) in pyridine (20 mL) was added EDC (341 mg, 1.78 mmol), and the mixture was stirred at room temperature overnight. The reaction mixture was concentrated under reduced pressure, and to it an aqueous NaHCO$_3$ solution (20 mL) was added. The mixture was extracted with 5% MeOH in CH$_2$Cl$_2$ (30 mL×3), and the organic layer was dried (MgSO$_4$) and evaporated under reduced pressure. The crude product was purified by MPLC on silica gel (4% MeOH in CH$_2$Cl$_2$) to afford the titled compound (482 mg, 84%) as a pale yellow solid.

$^1$H NMR (CDCl$_3$/TMS) δ 1.34 (t, 3H, J=7.2 Hz), 2.60 (apparent t, 4H, J=5.1 Hz), 3.30 (apparent t, 4H, J=5.1 Hz), 3.57 (s, 2H), 4.26 (q, 2H, J=7.2 Hz), 4.64 (d, 2H, J=5.7 Hz), 6.32 (br t, 1H, J=5.7 Hz), 6.41 (d, 1H, J=15.9 Hz), 6.88 (m, 2H), 7.27 (m, 1H), 7.36 (d, 2H, J=8.1 Hz), 7.49 (d, 2H, J=8.1 Hz), 7.64-7.72 (m, 4H), 8.53 (m, 1H), 8.57 (m, 1H)

(1-3) N-[4-(2-Hydroxycarbamoylvinyl)benzyl]-4-(4-pyridin-3-ylmethylpiperazin-1-yl)benzamide To a solution of 1.76 M NH$_2$OH in MeOH (1.23 mL) was added the compound (150 mg, 0.31 mmol) from the process (1-2), and the mixture was stirred at room temperature for 24 hours. The reaction mixture was concentrated, and the residue was dissolved in 1 N HCl aqueous solution (pH 5). The solid precipitated was collected by filtration, dried under vacuum, and crystallized from MeOH/CH$_2$Cl$_2$/ether to afford the titled compound (67 mg, 46%) as a pale brown solid.

$^1$H NMR (DMSO-d$_6$) δ 2.56 (m, 4H), 3.28 (m, 4H), 3.62 (br s, 2H), 4.45 (d, 2H, J=5.7 Hz), 6.42 (d, 1H, J=15.9 Hz), 6.96 (m, 2H), 7.31 (d, 2H, J=8.1 Hz), 7.37-7.45 (m, 2H), 7.50 (d, 2H, J=8.1 Hz), 7.76-7.79 (m, 3H), 8.50 (m, 1H), 8.54 (m, 1H), 8.78 (br t, 1H, J=5.7 Hz), 9.01 (br s, 1H), 10.73 (br s, 1H)

Example 2

N-[4-(2-Hydroxycarbamoylvinyl)benzyl]-4-(4-pyridin-2-ylmethylpiperazin-1-yl)benzamide The titled compound was prepared as described in Example 1 by using 1-(pyridin-2-ylmethyl)piperazine in place of 1-(pyridin-3-ylmethyl)piperazine.

(2-1) 4-(4-Pyridin-2-ylmethylpiperazin-1-yl)benzonitrile
yield: 32% (yellow solid)
$^1$H NMR (CDCl$_3$/TMS) δ 2.66 (apparent t, 4H, J=5.1 Hz), 3.36 (apparent t, 4H, J=5.1 Hz), 3.72 (s, 2H), 6.84 (m, 2H), 7.19 (m, 1H), 7.42 (m, 1H,), 7.48 (m, 2H), 7.68 (m, 1H), 8.59 (m, 1H)

(2-2) 3-(4-{[4-(4-Pyridin-2-ylmethylpiperazin 1-yl)benzoylamino]methyl}phenyl)acrylic acid ethyl ester
yield: 38% (off-white solid)
$^1$H NMR (DMSO-d$_6$) δ 1.25 (t, 3H, J=7.2 Hz), 2.57 (m, 4H), 3.28 (m, 4H), 3.66 (s, 2H), 4.18 (q, 2H, J=7.2 Hz), 4.46 (d, 2H, J=5.7 Hz), 6.59 (d, 1H, J=16.2 Hz), 6.96 (m, 2H), 7.26-7.34 (m, 3H), 7.48 (m, 1H), 7.60-7.68 (m, 3H), 7.75-7.81 (m, 3H), 8.51 (m, 1H), 8.80 (br t, 1H, J=5.7 Hz)

(2-3) N-[4-(2-Hydroxycarbamoylvinyl)benzyl]-4-(4-pyridin-2-ylmethylpiperazin-1-yl)benzamide
yield: 59% (off-pink solid)
$^1$H NMR (DMSO-d$_6$) δ 2.59 (m, 4H), 3.28 (m, 4H), 3.68 (br s, 2H), 4.45 (d, 2H, J=5.7 Hz), 6.42 (d, 1H, J=15.9 Hz), 6.96 (m, 2H), 7.26-7.34 (m, 3H), 7.43 (d, 1H, J=15.9 Hz), 7.47-7.52 (m, 3H), 7.77-7.81 (m, 3H), 8.51 (m, 1H), 8.78 (br t, 1H, J=5.7 Hz), 9.02 (br s, 1H), 10.73 (br s, 1H)

Example 3

N-[4-(2-Hydroxycarbamoylvinyl)benzyl]-4-(4-pyridin-4-ylmethylpiperazin-1-yl)benzamide The titled compound was prepared as described in Example 1 by using 1-(pyridin-4-ylmethyl)piperazine in place of 1-(pyridin-3-ylmethyl)piperazine.

(3-1) 4-(4-Pyridin-4-ylmethylpiperazin-1-yl)benzonitrile
yield: 59% (yellow solid)
$^1$H NMR (CDCl$_3$/TMS) δ 2.59 (apparent t, 4H, J=5.1 Hz), 3.35 (apparent t, 4H, J=5.1 Hz), 3.56 (s, 2H), 6.85 (m, 2H), 7.30 (m, 2H), 7.49 (m, 2H), 8.56 (m, 2H)

(3-2) 3-(4-{[4-(4-Pyridin-4-ylmethylpiperazin-1-yl)benzoylamino]methyl}phenyl)acrylic acid ethyl ester
yield: 94% (off-white solid)
$^1$H NMR (CDCl$_3$/TMS) δ 1.33 (t, 3H, J=7.2 Hz), 2.60 (apparent t, 4H, J=5.1 Hz), 3.31 (apparent t, 4H, J=5.1 Hz), 3.56 (s, 2H), 4.26 (q, 2H, J=7.2 Hz), 4.65 (d, 2H, J=5.7 Hz), 6.36 (br t, 1H, J=5.7 Hz), 6.41 (d, 1H, J=15.9 Hz), 6.88 (m, 2H), 7.30 (d, 2H, J=6.0 Hz), 7.36 (d, 2H, J=8.1 Hz), 7.49 (d, 2H, J=8.1 Hz), 7.66 (d, 1H, J=15.9 Hz), 7.72 (m, 2H) 8.56 (m, 2H)

(3-3) N-[4-(2-Hydroxycarbamoylvinyl)benzyl]-4-(4-pyridin-4-ylmethylpiperazin-1-yl)benzamide
yield: 54% (pale brown solid)
$^1$H NMR (DMSO-d$_6$) δ 2.52 (m, 4H), 3.28 (m, 4H), 3.57 (s, 2H), 4.45 (d, 2H, J=5.7 Hz), 6.42 (d, 1H, J=15.9 Hz), 6.96 (m, 2H), 7.32 (d, 2H, J=8.1 Hz), 7.36 (d, 2H, J=6.0 Hz), 7.42 (d, 1H, J=15.9 Hz), 7.51 (d, 2H, J=8.1 Hz), 7.78 (m, 2H), 8.53 (d, 2H, J=(6.0 Hz), 8.78 (br t, 1H, J=5.7 Hz), 9.02 (br s, 1H), 10.73 (br s, 1H)

Example 4

N-[4-(2-Hydroxycarbamoylvinyl)benzyl]picolinamide

The titled compound was prepared in a similar manner to the process described in Example 1 by using picolinic acid.

(4-1) 3-{4-[(Picolinoylamino)methyl]phenyl}acrylic acid ester
yield: 58% (pale yellow oil)
$^1$H NMR (CDCl$_3$/TMS) δ 1.34 (t, 3H, J=7.2 Hz), 4.26 (q, 2H, J=7.2 Hz), 4.69 (d, 2H, J=6.3 Hz), 6.42 (d, 1H, J=15.9 Hz), 7.38 (d, 2H, J=8.1 Hz), 7.44 (m, 1H), 7.50 (d, 2H, J=8.1 Hz), 7.67 (d, 1H, J=15.9 Hz), 7.87 (m, 1H), 8.24 (m, 1H), 8.42 (m, 1H), 8.54 (m, 1H)

(4-2) N-[4-(2-Hydroxycarbamoylvinyl)benzyl]picolinamide
yield: 29% (off-white solid)
$^1$H NMR (DMSO-d$_6$) δ 4.51 (m, 2H), 6.45 (d, 1H, J=15.9 Hz), 7.35 (d, 2H, J=8.1 Hz), 7.42 (d, 1H, J=15.9 Hz), 7.50 (d, 2H, J=8.1 Hz), 7.59-7.64 (m, 1H), 7.97-8.06 (m, 2H), 8.66 (m, 1H), 9.02 (br s, 1H), 9.36 (m, 1H), 10.76 (br s, 1H)

Example 5

N-[4-(2-Hydroxycarbamoylvinyl)benzyl]-4-pyrrolidin-1-ylbenzamide (5-1) N-(4-Hydroxymethylbenzyl)-4-pyrrolidin-1-ylbenzamide To a mixture of 4-pyrrolidin-1-ylbenzoic acid (2.0 g, 10.5 mmol), (4-aminomethylphenyl)methanol (4.3 g, 31.4 mmol), 1-hydroxybenzotriazole (1.7 g, 12.6 mmol), and DMAP (256 mg, 2.1 mmol) in pyridine (50 mL) was added EDC (3.0 g, 15.7 mmol), and the mixture was stirred at room temperature overnight. The reaction mixture was concentrated under reduced pressure, and an aqueous NaHCO$_3$ solution (50 mL) was added. The mixture was extracted with 5% MeOH in CHCl$_3$ (150 mL×2), and the organic layer was dried (MgSO$_4$) and evaporated under reduced pressure. The crude product was purified by MPLC on silica gel (3% MeOH in CHCl$_3$) to afford the titled compound (2.56 g, 79%) as a white solid.

$^1$H NMR (DMSO-d$_6$) δ 1.96 (m, 4H), 3.28 (m, 4H), 4.41-4.47 (m, 4H), 5.10 (t, 1H, J=5.7 Hz), 6.53 (m, 2H), 7.25 (apparent s, 4H), 7.75 (m, 2H), 8.59 (br t, 1H, J=6.0 Hz)

(5-2) 3-{4-[(4-Pyrrolidin-1-ylbenzoylamino)methyl]phenyl}acrylic acid ethyl ester To a solution of oxalyl chloride (0.93 mL, 10.6 mmol) in THF (10 mL) at −78° C. was added a solution of DMSO (1.65 mL, 23.2 mmol) in THF (10 mL), and the reaction mixture was stirred for 30 minutes. A solution of the compound (1.5 g, 4.8 mmol) from the process (5-1) in THF (200 mL) was added to it, and then the mixture was stirred for 1 hour and warmed to −35° C. After 10 minutes, the mixture was cooled to −78° C., and triethylamine (3.37 mL, 24.2 mmol) was added. After stirring at 0° C. for 1 hour, the mixture was diluted with water (150 mL), and then THF was evaporated under reduced pressure. The resulting residue was extracted with 5% MeOH in CHCl$_3$ (250 mL×2). The extract was dried (MgSO$_4$) and evaporated to dryness under reduced pressure to give a crude product which was crystallized from MeOH/CHCl$_3$/ether to afford the corresponding aldehyde (925 mg, 62%) as a white solid.

A solution of the aldehyde (1.35 g, 4.38 mmol) above, (Ph)$_3$P=CHCO$_2$Et (2.29 g, 6.57 mmol) in CH$_3$CN (60 mL) was stirred at 70° C. for 2 hours. The reaction mixture was concentrated under reduced pressure, and the residue was purified by MPLC on silica gel (2% MeOH in CHCl$_3$) to afford the titled compound (1.25 g, 76%) as a pale yellow solid.

$^1$H NMR (DMSO-d$_6$) δ 1.25 (t, 3H, J=7.2 Hz), 1.96 (m, 4H), 3.28 (m, 4H), 4.18 (q, 2H, J=7.2 Hz), 4.46 (d, 2H, J=5.7 Hz), 6.54 (m, 2H), 6.58 (d, 1H, J=16.5 Hz), 7.33 (d, 2H, J=8.1 Hz), 7.62 (d, 1H, J=16.5 Hz), 7.67 (d, 2H, J=8.1 Hz), 7.76 (m, 2H), 8.66 (br t, 1H, J=5.7 Hz)

(5-3) N-[4-(2-Hydroxycarbamoylvinyl)benzyl]-4-pyrrolidin-1-ylbenzamide

The titled compound was prepared as described in the process (1-3) by using the compound from the process (5-2).
yield: 35% (pale brown solid)
$^1$H NMR (DMSO-d$_6$) δ 1.96 (m, 4H), 3.28 (m, 4H), 4.45 (d, 2H, J=5.7 Hz), 6.42 (d, 1H, J=15.9 Hz), 6.54 (m, 2H), 7.32 (d, 2H, J=8.1 Hz), 7.43 (d, 1H, J=15.9 Hz), 7.50 (d, 2H, J=8.1 Hz), 7.76 (m, 2H), 8.64 (br t, 1H, J=5.7 Hz), 9.00 (br s, 1H), 10.70 (br s, 1H)

Example 6

4-Dimethylamino-N-[4-(2-hydroxycarbamoylvinyl)benzyl]benzamide

The titled compound was prepared as described in Example 5 by using 4-(dimethylamino)benzoic acid in place of 4-pyrrolidin-1-ylbenzoic acid.

(6-1) 4-Dimethylamino-N-(4-hydroxymethylbenzyl)benzamide

To a mixture of 4-(dimethylamino)benzoic acid (915 mg, 5.54 mmol) and triethylamine (772 μL, 5.54 mmol) in CH$_2$Cl$_2$ (25 mL) at 0° C. was added BOP-Cl (1.50 g, 6.09 mmol), and the mixture was stirred at room temperature for 20 minutes. To the reaction mixture was added (4-aminomethylphenyl)methanol (760 mg, 5.54 mmol) and triethylamine (1.54 mL, 11.08 mmol), and the mixture was stirred at room temperature overnight. To the reaction mixture was added a 50% aqueous NaHCO$_3$ solution (50 mL), and the mixture was extracted with 5% MeOH in CHCl$_3$ (100 mL×1, 40 mL×2). The organic layer was dried (MgSO$_4$) and evaporated under reduced pressure. The crude product was purified by MPLC on silica gel (2% MeOH in CHCl$_3$) to afford the titled compound (1.04 g, 66%) as a white solid.

$^1$H NMR (DMSO-d$_6$) δ 2.97 (s, 6H), 4.41-4.47 (m, 4H), 5.10 (t, 1H, J=5.7 Hz), 6.70 (m, 2H), 7.25 (apparent s, 4H), 7.76 (m, 2H), 8.63 (br t, 1H, J=6.0 Hz)

(6-2) 3-{4-[(4-Dimethylaminobenzoylamino)methyl]phenyl}acrylic acid ethyl ester
yield: 74% (white solid)
$^1$H NMR (DMSO-d$_6$) δ 1.25 (t, 3H, J=7.2 Hz), 2.97 (s, 6H), 4.18 (q, 2H, J=7.2 Hz), 4.46 (d, 2H, J=6.0 Hz), 6.59 (d, 1H, J=15.9 Hz), 6.71 (m, 2H), 7.33 (d, 2H, J=8.1 Hz), 7.63 (d, 1H, J=15.9 Hz), 7.67 (d, 2H, J=8.1 Hz), 7.77 (m, 2H), 8.70 (br t, 1H, J=6.0 Hz)

(6-3) 4-Dimethylamino-N-[4-(2-hydroxycarbamoylvinyl)benzyl]benzamide
yield: 58% (pale pink solid)
$^1$H NMR (DMSO-d$_6$) δ 2.97 (s, 6H), 4.45 (d, 2H, J=5.7 Hz), 6.42 (d, 1H, J=15.9 Hz), 6.71 (m, 2H), 7.33 (d, 2H, J=8.1 Hz), 7.43 (d, 1H, J=15.9 Hz), 7.51 (d, 2H, J=8.1 Hz), 7.77 (m, 2H), 8.68 (br t, 1H, J=5.7 Hz), 9.00 (br s, 1H), 10.71 (br s, 1H)

Example 7

N-[4-(2-Hydroxycarbamoylvinyl)benzyl]nicotinamide

The titled compound was prepared as described in Example 5 by using nicotinic acid in place of 4-pyrrolidin-1-ylbenzoic acid.

(7-1) N-(4-Hydroxymethylbenzyl)nicotinamide
yield: 86% (white solid)
$^1$H NMR (DMSO-d$_6$) δ 4.46-4.49 (m, 4H), 5.13 (br t, 1H, J=5.6 Hz), 7.28 (apparent s, 4H), 7.51 (dd, 1H, J=7.8 Hz, 4.8 Hz), 8.22 (m, 1H), 8.71 (dd, 1H, J=4.8 Hz, 1.5 Hz), 9.04 (d, 1H, J=2.1 Hz), 9.21 (br t, 1H, J=5.7 Hz)

(7-2) 3-{4-[(Nicotinoylamino)methyl]phenyl}acrylic acid ethyl ester
yield: 39% (pale yellow solid)
$^1$H NMR (DMSO-d$_6$) δ 1.26 (t, 3H, J=7.2 Hz), 4.19 (q, 2H, J=7.2 Hz), 4.53 (d, 2H, J=6.0 Hz), 6.60 (d, 1H, J=15.9 Hz), 7.38 (d, 2H, J=8.1 Hz), 7.52 (m, 1H), 7.63 (d, 1H, J=15.9 Hz), 7.69 (d, 2H, J=8.1 Hz), 8.23 (m, 1H), 8.72 (m, 1H), 9.06 (m, 1H), 9.26 (br t, 1H, J=6.0 Hz)

(7-3) N-[4-(2-Hydroxycarbamoylvinyl)benzyl]nicotinamide
yield: 74% (pale pink solid)
$^1$H NMR (DMSO-d$_6$) δ 4.51 (m, 2H), 6.43 (d, 1H, J=15.9 Hz), 7.37 (d, 2H, J=8.1 Hz), 7.44 (d, 1H, J=15.9 Hz), 7.52 (m, 1H), 7.53 (d, 2H, J=8.1 Hz), 8.23 (m, 1H), 8.72 (m, 1H), 9.05 (m, 1H), 9.25 (m, 1H)

Example 8

[4-(2-Hydroxycarbamoylvinyl)benzyl]carbamic acid pyridin-3-ylmethyl ester (8-1) (4-Hydroxymethylbenzyl)carbamic acid pyridin-3-ylmethyl ester
To a solution of N,N-carbonyldiimidazole (2.1 g, 12.8 mmol) in THF (15 mL) was added a solution of 3-pyridylcarbinol (1.3 g, 11.6 mmol) in THF (15 mL). After stirring for 30 minutes, a solution of (4-aminomethylphenyl)methanol (1.4 g, 10.4 mmol) in THF (15 mL) and triethylamine (3.2 mL, 23.2 mmol) were added, and the mixture was stirred overnight. The reaction mixture was concentrated under reduced pressure, and the residue was diluted with water (30 mL) and extracted with 10% MeOH in CHCl$_3$ (30 mL×2). The organic layer was dried (Na$_2$SO$_4$), evaporated under reduced pressure, and the residue was purified by MPLC on silica gel (5% MeOH in CHCl$_3$) to afford the titled compound (1.31 g, 46%) as a white solid.
$^1$H NMR (DMSO-d$_6$) δ 4.18 (m, 2H), 4.45 (s, 2H), 5.08 (s, 2H), 7.19 (d, 2H, J=8.0 Hz), 7.25 (d, 2H, J=8.0 Hz), 7.40 (m, 1H), 7.77 (m, 1H), 7.83 (m, 1H), 8.52 (m, 1H), 8.58 (m, 1H)

(8-2) 3-{4-[(pyridin-3-ylmethoxycarbonylamino)methyl]phenyl}acrylic acid methyl ester
The titled compound was prepared as described in the process (5-2) using the compound from the process (8-1).
yield: 75% (white solid)
$^1$H NMR (DMSO-d$_6$) δ 3.72 (s, 3H), 4.23 (d, 2H, J=6.0 Hz), 5.09 (s, 2H), 6.61 (d, 1H, J=15.9 Hz), 7.29 (d, 2H, J=8.1 Hz), 7.40 (m, 1H), 7.64 (d, 1H, J=15.9 Hz), 7.67 (d, 2H, J=8.1 Hz), 7.78 (m, 1H), 7.90 (br t, 1H, J=6.0 Hz), 8.53 (m, 1H), 8.58 (m, 1H)

(8-3) [4-(2-Hydroxycarbamoylvinyl)benzyl]carbamic acid pyridin-3-ylmethyl ester
The titled compound was prepared as described in the process (1-3) using the compound from the process (8-2).
yield: 39% (pale pink solid)
$^1$H NMR (DMSO-d$_6$) δ 4.21 (m, 2H), 5.09 (s, 2H), 6.43 (d, 1H, J=15.9 Hz), 7.28 (m, 2H), 7.40 (m, 1H), 7.43 (d, 1H, J=15.9 Hz), 7.51 (m, 2H), 7.78 (m, 1H), 7.89 (m, 1H), 8.53 (m, 1H), 8.59 (m, 1H)

Example 9

N-Hydroxy-3-[4-(pyridin-3-ylsulfamoylmethyl)phenyl]acrylamide (9-1) 4-(Pyridin-3-ylsulfamoylmethyl)benzoic acid methyl ester
To a solution of 4-chlorosulfonylmethylbenzoic acid methyl ester (435 mg, 1.75 mmol) and 3-aminopyridine (170 mg, 1.81 mmol) in CH$_2$Cl$_2$ (10 mL) at 0° C. was added triethylamine (488 μL, 3.50 mmol), and the reaction mixture was stirred at room temperature for 2 hours. The reaction mixture was diluted with CHCl$_3$, and the mixture was washed with water and brine. The organic layer was dried (Na$_2$SO$_4$) and evaporated under reduced pressure to give the crude product which was purified by MPLC on silica gel (3% MeOH in EtOAc) to afford the titled compound (434 mg, 81%) as a white solid.
$^1$H NMR (DMSO-d$_6$) δ 3.86 (s, 3H), 4.68 (s, 2H), 7.32 (dd, 1H, J=8.4 Hz, 4.8 Hz), 7.45 (d, 2H, J=8.1 Hz), 7.55 (m, 1H), 7.93 (d, 2H, J=8.1 Hz), 8.28 (dd, 1H, J=4.8 Hz, 1.5 Hz), 8.36 (d, 1H, J=1.8 Hz), 10.13 (br s, 1H)

(9-2) C-(4-Hydroxymethylphenyl)-N-pyridin-3-ylmethanesulfonamide
To a solution of 4-(pyridin-3-ylsulfamoylmethyl)benzoic acid methyl ester (1.91 g, 6.23 mmol) in THF (60 mL) at 0° C. was added a 1 M solution of LiAlH$_4$ in THF (13.7 mL, 13.7 mmol), and the mixture was warmed to room temperature. After stirring for 10 minutes, the mixture was heated to reflux temperature for 3 hours. The reaction mixture was cooled to 0° C. and quenched with saturated Na$_2$SO$_4$ aqueous solution (1.9 mL). The mixture was neutralized with 1 N HCl solution (13.7 mL), and then THF was evaporated under reduced pressure. The residue was diluted with water (70 mL) and extracted with CHCl$_3$ (50 mL×3). The organic layer was washed with brine, dried (Na$_2$SO$_4$) and concentrated under reduced pressure. The residue was purified by MPLC on silica gel (6% MeOH in EtOAc) to afford the titled compound (1.43 g, 83%) as a pale yellow solid.
$^1$H NMR (DMSO-d$_6$) δ 4.48 (s, 2H), 4.50 (s, 2H), 7.22 (d, 2H, J=8.1 Hz), 7.29 (d, 2H), J=8.1 Hz), 7.32 (m, 1H), 7.55 (m, 1H), 8.26 (m, 1H), 8.36 (m, 1H)

(9-3) 3-[4-(Pyridin-3-ylsulfamoylmethyl)phenyl]acrylic acid ethyl ester
The titled compound was prepared as described in the process (5-2) using the compound from the process (9-2).
yield: 53% (white solid)
$^1$H NMR (DMSO-d$_6$) δ 1.27 (t, 3H, J=7.2 Hz), 4.20 (q, 2H, J=7.2 Hz), 4.60 (s, 2H), 6.64 (d, 1H, J=15.9 Hz), 7.31 (m, 1H), 7.33 (d, 2H, J=8.1 Hz), 7.55 (m, 1H), 7.63 (d, 1H, J=15.9 Hz), 7.70 (d, 2H, J=8.1 Hz), 8.27 (m, 1H), 8.36 (m, 1H), 10.20 (br s, 1H)

(9-4) N-Hydroxy-3-[4-(pyridin-3-ylsulfamoylmethyl)phenyl]acrylamide
The titled compound was prepared as described in the process (1-3) using the compound from the process (9-3).
yield: 64% (white solid)
$^1$H NMR (DMSO-d$_6$) δ 4.59 (s, 2H), 6.46 (d, 1H, J=15.9 Hz), 7.30-7.34 (m, 3H), 7.44 (d, 1H, J=15.9 Hz), 7.52-7.57 (m, 3H), 8.28 (m, 1H), 8.37 (m, 1H), 9.04 (br s, 1H), 10.08 (br s, 1H), 10.75 (br s, 1H)

Example 10

3-[4-(Benzenesulfonylmethyl)phenyl]-N-hydroxyacrylamide (10-1) 4-(Phenylsulfanylmethyl)benzoic acid methyl ester
To a mixture of benzenethiol (1.3 mL, 13.1 mmol) and potassium tert-butoxide (1.47 g, 13.1 mmol) in DMF (50 mL) at 0° C. was added 4-(bromomethyl)benzoic acid methyl ester (3.0 g, 13.1 mmol), and the mixture was stirred at room temperature for 1 hour. After stirring at 80-90° C. overnight, the reaction mixture was evaporated to dryness under reduced pressure. The residue was dissolved in water (30 mL) and extracted with CH$_2$Cl$_2$ (200 mL). The organic layer was dried (MgSO$_4$) and evaporated under reduced pressure. The crude product was purified by MPLC on silica gel (10% EtOAc in hexanes) to afford the titled compound (2.74 g, 81%) as a white solid.

¹H NMR (CDCl₃/TMS) δ 3.90 (s, 3H), 4.12 (s, 2H), 7.19-7.30 (m, 5H), 7.32 (d, 2H, J=8.1 Hz), 7.94 (d, 2H, J=8.1 Hz)

(10-2) 4-(Benzenesulfonylmethyl)benzoic acid methyl ester

To a mixture of the compound (2.5 g, 9.68 mmol) from the process (10-1) in a 50% aqueous solution of methanol (60 mL) at 0° C. was added OXONE (12.5 g, 20.32 mmol), and the mixture was stirred at room temperature overnight. To the reaction mixture was added an aqueous NaHCO₃ solution (25 mL), and the mixture was extracted with CH₂Cl₂ (250 mL). The organic layer was dried (MgSO₄) and evaporated under reduced pressure. The crude product was purified by MPLC on silica gel (1% MeOH in CHCl₃) to afford the titled compound (2.36 g, 84%) as a white solid.

¹H NMR (CDCl₃/TMS) δ 3.84 (s, 3H), 4.81 (s, 2H), 7.29 (d, 2H, J=8.1 Hz), 7.57-7.62 (m, 2H), 7.69-7.72 (m, 3H), 7.86 (d, 2H, J=8.1 Hz)

(10-3) [4-(Benzenesulfonylmethyl)phenyl]methanol

To a solution of the compound (2.3 g, 7.92 mmol) from the process (10-2) in CH₂Cl₂ (50 mL) at −78° C. was added slowly DIBAL-H (1 M in toluene, 16.6 mL, 16.63 mmol), and the mixture was stirred at room temperature for 2 hours. The reaction mixture was cooled to 0° C., and to it an aqueous NH₄Cl solution (250 mL) was added slowly. The mixture was extracted with 10% MeOH in CH₂Cl₂ (1.5 L), and the organic layer was dried (MgSO₄) and evaporated under reduced pressure. The crude product was crystallized from MeOH/CH₂Cl₂/ether to afford the titled compound (1.66 g, 80%) as white solid.

¹H NMR (DMSO-d₆) δ 4.45 (s, 2H), 4.64 (s, 2H), 7.08 (d, 2H, J=8.1 Hz), 7.21 (d, 2H, J=8.1 Hz), 7.56-7.61 (m, 2H), 7.69-7.73 (m, 3H)

(10-4) 3-[4-(Benzenesulfonylmethyl)phenyl]acrylic acid ethyl ester

The titled compound was prepared as described in the process (5-2) using the compound from the process (10-3).

yield: 82% (white solid)

¹H NMR (DMSO-d₆) δ 3.72 (s, 3H), 4.73 (s, 2H), 6.64 (d, 1H, J=15.9 Hz), 7.18 (d, 2H, J=8.1 Hz), 7.57-7.65 (m, 5H), 7.70-7.74 (m, 3H)

(10-5) 3-[4-(Benzenesulfonylmethyl)phenyl]-N-hydroxyacrylamide

The titled compound was prepared as described in the process (1-3) using the compound from the process (10-4).

yield: 52% (pale red solid)

¹H NMR (DMSO-d₆) δ 4.71 (s, 2H), 6.45 (d, 1H, J=15.9 Hz), 7.17 (d, 2H, J=8.1 Hz), 7.41 (d, 1H, J=15.9 Hz), 7.47 (d, 2H, J=8.1 Hz), 7.57-7.62 (m, 2H), 7.71-7.74 (m, 3H), 9.04 (br s, 1H), 10.75 (br s, 1H)

Example 11

N-Hydroxy-3-[4-(pyridine-2-sulfonylmethyl)phenyl]acrylamide

The titled compound was prepared as described in Example 10 by using 2-mercaptopyridine in place of benzenethiol.

(11-1) 4-(Pyridine-2-sulfanylmethyl)benzoic acid methyl ester yield: 76% (white solid)

¹H NMR (CDCl₃/TMS) δ 3.89 (s, 3H), 4.48 (s, 2H), 6.99 (m, 1H), 7.15 (m, 1H), 7.44-7.50 (m, 3H), 7.95 (d, 2H, J=8.1 Hz), 8.45 (m, 1H)

(11-2) 4-(Pyridine-2-sulfonylmethyl)benzoic acid methyl ester yield: 98% (white solid)

¹H NMR (CDCl₃/TMS) δ 3.83 (s, 3H), 4.94 (s, 2H), 7.34 (d, 2H, J=8.4 Hz), 7.76 (m, 1H), 7.84 (m, 1H), 7.86 (d, 2H, J=8.4 Hz), 8.07 (m, 1H), 8.85 (m, 1H)

(11-3) [4-(Pyridine-2-sulfonylmethyl)phenyl]methanol yield: 79% (white solid)

¹H NMR (DMSO-d₆) δ 4.44 (s, 2H), 4.78 (s, 2H), 7.12 (d, 2H, J=8.1 Hz), 7.21 (d, 2H, J=8.1 Hz), 7.75 (m, 1H), 7.84 (m, 1H), 8.07 (m, 1H), 8.86 (m, 1H)

(11-4) 3-[4-(Pyridine-2-sulfonylmethyl)phenyl]acrylic acid methyl ester yield: 84% (pale yellow solid)

¹H NMR (DMSO-d₆) δ 3.72 (s, 3H), 4.87 (s, 2H), 6.63 (d, 1H, J=15.8 Hz), 7.23 (d, 2H, J=8.1 Hz), 7.61 (d, 1H, J=15.8 Hz), 7.64 (d, 2H, J=8.1 Hz), 7.76 (m, 1H), 7.86 (m, 1H), 8.08 (m, 1H), 8.86 (m, 1H)

(11-5) N-Hydroxy-3-[4-(pyridine-2-sulfonylmethyl)phenyl]acrylamide yield: 42% (pale red solid)

¹H NMR (DMSO-d₆) δ 4.85 (s, 2H), 6.43 (d, 1H, J=16.2 Hz), 7.21 (d, 2H, J=8.1 Hz), 7.40 (d, 1H, J=16.2 Hz), 7.47 (d, 2H, J=8.1 Hz), 7.76 (m, 1H), 7.85 (m, 1H), 8.08 (m, 1H), 8.86 (m, 1H), 9.04 (br s, 1H), 10.74 (br s, 1H)

Example 12

N-Hydroxy-3-[4-(pyridine-4-sulfonylmethyl)phenyl]acrylamide

The titled compound was prepared as described in Example 10 by using 4-mercaptopyridine in place of benzenethiol.

(12-1) 4-(Pyridine-4-sulfanylmethyl)benzoic acid methyl ester yield: 77% (pale yellow solid)

¹H NMR (CDCl₃/TMS) δ 3.91 (s, 3H), 4.24 (s, 2H), 7.09 (m, 1H), 7.47 (d, 2H, J=8.1 Hz), 8.01 (d, 2H, J=8.1 Hz), 8.38 (m, 1H)

(12-2) 4-(Pyridine-4-sulfonylmethyl)benzoic acid methyl ester yield: 71% (white solid)

¹H NMR (CDCl₃/TMS) δ 3.93 (s, 3H), 4.39 (s, 2H), 7.20 (d, 2H, J=8.1 Hz), 7.48 (m, 1H), 7.97 (d, 2H, J=8.1 Hz), 8.81 (m, 1H)

(12-3) [4-(Pyridine-4-sulfonylmethyl)phenyl]methanol yield: 69% (white solid)

¹H NMR (DMSO-d₆) δ 4.46 (s, 2H), 4.74 (s, 2H), 7.13 (d, 2H, J=8.1 Hz), 7.24 (d, 2H, J=8.1 Hz), 7.70 (m, 2H), 8.87 (m, 2H)

(12-4) 3-[4-(Pyridine-4-sulfonylmethyl)phenyl]acrylic acid ethyl ester yield: 51% (white solid)

¹H NMR (DMSO-d₆) δ 1.34 (t, 3H, J=7.2 Hz), 4.27 (q, 2H, J=7.2 Hz), 4.36 (s, 2H), 6.44 (d, 1H, J=15.9 Hz), 7.15 (d, 2H, J=8.1 Hz), 7.45 (d, 2H, J=8.1 Hz), 7.50 (m, 2H), 7.64 (d, 1H, J=15.9 Hz), 8.82 (m, 2H)

(12-5) N-Hydroxy-3-[4-(pyridine-4-sulfonylmethyl)phenyl]acrylamide yield: 45% (red solid)

¹H NMR (DMSO-d₆) δ 4.88 (s, 2H), 6.46 (d, 1H, J=15.3 Hz), 7.21 (d, 2H, J=8.1 Hz), 7.36 (d, 1H, J=15.3 Hz), 7.49 (d,

2H, J=8.1 Hz), 7.70 (d, 1H, J=5.4 Hz), 8.88 (d, 1H, J=5.4 Hz), 9.07 (br s, 1H), 10.76 (br s, 1H)

Example 13

Naphthalene-2-carboxylic acid 4-(2-hydroxycarbamoylvinyl)benzylamide (13-1) 3-(4-{[(Naphthalene-2-carbonyl)amino]methyl}phenyl)acrylic acid ethyl ester The titled compound was prepared as described in the process (1-2) by using 2-naphthoic acid.

yield: 82% (white solid)

$^1$H NMR (DMSO-$d_6$) δ 1.25 (t, 3H, J=7.2 Hz), 4.18 (q, 2H, J=7.2 Hz), 4.56 (m, 2H), 7.60 (d, 1H, J=15.9 Hz), 7.40 (d, 2H, J=8.1 Hz), 7.57-7.71 (m, 5H), 7.97-8.05 (m, 4H), 8.51 (s, 1H), 9.24 (br t, 1H, J=6.0 Hz)

(13-2) Naphthalene-2-carboxylic acid 4-(2-hydroxycarbamoylvinyl)benzylamide

The titled compound was prepared as described in the process (1-2) by using the compound from the process (13-1).

yield: 85% (pale pink solid)

$^1$H NMR (DMSO-$d_6$) δ 4.55 (m, 2H), 6.44 (d, 1H, J=15.6 Hz), 7.38-7.65 (m, 7H), 7.97-8.04 (m, 4H), 8.51 (s, 1H), 9.23 (m, 1H)

Example 14

Quinoline-3-carboxylic acid 4-(2-hydroxycarbamoylvinyl)benzylamide (14-1) 3-(4-{[(Quinoline-3-carbonyl)amino]methyl}phenyl)acrylic acid ethyl ester The titled compound was prepared as described in the process (1-2) by using 3-quinolinecarboxylic acid.

yield: 89% (white solid)

$^1$H NMR (DMSO-$d_6$) δ 1.25 (t, 3H, J=7.2 Hz), 4.18 (q, 2H, J=7.2 Hz), 4.58 (d, 2H, J=5.7 Hz), 6.61 (d, 1H, J=15.9 Hz), 7.43 (d, 2H, J=8.4 Hz), 7.64 (d, 1H, J=15.9 Hz), 7.68-7.72 (m, 3H), 7.85-7.90 (m, 1H), 8.08-8.12 (m, 2H), 8.88 (m, 1H), 9.33 (m, 1H), 9.42 (br t, 1H, J=5.7 Hz)

(14-2) Quinoline-3-carboxylic acid 4-(2-hydroxycarbamoylvinyl)benzylamide

The titled compound was prepared as described in the process (1-2) by using the compound from the process (14-1).

yield: 89% (pale pink solid)

$^1$H NMR (DMSO-$d_6$) δ 4.58 (d, 2H, J=5.1 Hz), 6.45 (d, 1H, J=15.9 Hz), 7.42 (d, 2H, J=8.1 Hz), 7.43-7.56 (m, 3H), 7.70 (m, 1H), 7.88 (m, 1H), 8.10 (d, 2H, J=8.1 Hz), 8.89 (m, 1H), 9.01 (br s, 1H), 9.33 (m, 1H), 9.42 (m, 1H), 10.74 (br s, 1H)

Example 15

Quinoline-2-carboxylic acid 4-(2-hydroxycarbamoylvinyl)benzylamide

The titled compound was prepared as described in Example 5 by using 2-quinolinecarboxylic acid in place of 4-pyrrolidin-1ylbenzoic acid.

(15-1) Quinoline-2-carboxylic acid 4-hydroxymethylbenzylamide yield: 82% (white solid)

$^1$H NMR (CDCl$_3$/TMS) δ 1.90 (m, 1H), 4.69 (d, 2H, J=5.1 Hz), 4.72 (d, 2H, J=6.3 Hz), 7.35 (d, 2H, J=8.1 Hz), 7.40 (d, 2H, J=8.1 Hz), 7.61 (m, 1H), 7.74 (m, 1H), 7.88 (m, 1H), 8.06 (m, 1H), 8.32 (m, 2H), 8.61 (m, 1H)

(15-2) 3-(4-{[(Quinoline-2-carbonyl)amino]methyl}phenyl)acrylic acid ethyl ester yield: 91% (white solid)

$^1$H NMR (CDCl$_3$/TMS) δ 1.34 (t, 3H, J=7.2 Hz), 4.26 (q, 2H, J=7.2 Hz), 4.76 (d, 2H, J=6.3 Hz), 6.43 (d, 1H, J=15.9 Hz), 7.43 (d, 2H, J=8.1 Hz), 7.52 (d, 2H, J=8.1 Hz), 7.60-7.71 (m, 2H), 7.76 (m, 1H), 7.89 (m, 1H), 8.08 (m, 1H), 8.34 (m, 2H), 8.65 (m, 1H)

(15-3) Quinoline-2-carboxylic acid 4-(2-hydroxycarbamoylvinyl)benzylamide yield: 92% (pale brown solid)

$^1$H NMR (DMSO-$d_6$) δ 4.58 (d, 2H, J=6.3 Hz), 6.43 (d, 1H, J=15.9 Hz), 7.39-7.46 (m, 3H), 7.53 (d, 2H, J=8.1 Hz), 7.73 (m, 1H), 7.88 (m, 1), 8.08-8.19 (m, 3H), 8.58 (m, 1H), 9.02 (br s, 1H), 9.51 (br t, 1H, J=6.3 Hz), 10.72 (br s, 1H)

Example 16

In Vitro Cytotoxicity

Three human cancer cell lines (A-549, lung cancer; SK-BR-3, breast cancer; MKN-45, stomach cancer) were tested in MTT assay. These cell lines were grown in RPMI 1640 medium supplemented with penicillin-streptomycin (100 units/mL) and 10% heat-inactivated fetal bovine serum under standard culture condition (20% $O_2$ and 5% $CO_2$, 37° C.). Single-cell suspensions were prepared by trypsinization and pipette disaggregation. The number of cells for each cell line plated in 96-well microtiter plates was determined from the growth curve obtained in MTT assay. Test compounds were diluted from stock solution in DMSO into fresh medium to a 10× concentration. Cells were inoculated into each well in 180 μL of medium and eight different concentrations of 20 μL of test compounds were added to each well. The plates were then incubated for 4 days at 37° C., 5% $CO_2$. After 4 days of culture, 0.1 mg (20 μL of 5 mg/mL) of MTT was added to each well. The plates were then incubated at 37° C. for 4 hours. After the plates were centrifuged at 1,000 rpm for 10 minutes, the supernatant was aspirated. 150 μL of DMSO was added to each well to solubilize formazan crystals. The plates were read immediately at 550 nm on Elisa reader (Dynatech, MR 5000). The IC$_{50}$ was defined as the concentration of compounds that produced a 50% reduction of surviving cells and calculated by quantal probit analysis of pharmacologic calculations with computer program.

TABLE 1

In vitro cytotoxicity of test compounds in the human cancer cell lines

| | IC$_{50}$ (μM) | | |
|---|---|---|---|
| Compound | A-549 | SK-BR-3 | MKN-45 |
| Example 1 | 11.98 | 3.19 | 38.59 |
| Example 2 | 1.65 | 0.27 | 2.94 |
| Example 3 | 3.02 | 1.72 | 56.06 |
| Example 4 | 2.23 | 0.87 | 3.64 |
| Example 5 | 0.35 | 0.11 | 0.80 |
| Example 6 | 0.48 | 0.16 | 0.83 |
| Example 7 | 2.89 | 1.28 | 4.98 |
| Example 8 | 2.61 | 1.12 | 3.34 |
| Example 9 | 36.96 | 22.90 | 61.97 |
| Example 10 | 11.08 | 4.57 | 8.34 |

Example 17

In Vitro Inhibition of Histone Deacetylase

Four human gastric adenocarcinoma cells (SNU-16, 601, 620 and 638) were obtained from the Korean Cell Line Bank and grown in RPMI 1640 medium supplemented with 10% heat-inactivated fetal bovine serum and gentamycin (10 μg/mL) under standard culture condition (20% $O_2$ and 5% $CO_2$, 37° C.). Test compounds were dissolved in DMSO and used at a final concentration of 1 μM.

Cells ($5 \times 10^6$) were cultured with and without a test compound (1 μM). Cells were pelleted and resuspended in 1 mL ice-cold lysis buffer (10 mM Tris-HCl, pH 6.5/50 mM sodium bisulfite/1% Triton X-100/10 mM $MgCl_2$/8.6% sucrose) before homogenization with two dounce strokes. Nuclei were centrifuged at 700 rpm for 5 minutes and washed 3 times with 1 mL of lysis buffer. The final wash was performed with 1 mL of Tris-EDTA solution (10 mM Tris-HCl, pH 7.4/13 mM EDTA). Nuclei were pelleted and resuspended in 100 μL of ice-cold water. Sulfuric acid was added to the samples to a final concentration of 0.2 M; samples were vortexed and incubated on ice for 1 hour. Samples were centrifuged at 13,000 rpm for 10 minutes at 4° C., and the supernatant was precipitated with 1 mL of acetone overnight at −20° C.

Precipitated protein was collected by centrifugation at 13,000 rpm for 10 minutes at 4-° C, air dried, and resuspended in 50-100 μL water. Proteins (20 μg protein) were denatured at 100° C. in loading buffer for 5 minutes and electrophoresed in 15% polyacrylamide gels. After electrophoresis, samples were transferred onto nitrocellulose (0.2 μm) and probed with antibody to acetylated histone H3 or H4 (Upstate Biotechnology Inc.) as recommended by the manufacturer. Detection was performed using enhanced chemiluminescence system (Amersham). To verify equal protein loading, a parallel protein gel was run and stained with coomassie blue.

What is claimed is:

1. A compound selected from the group consisting of N-[4-(2-Hydroxycarbamoylvinyl)benzyl]-4-pyrrolidin-1-ylbenzamide, and 4-Dimethylamino-N-[4-(2-hydroxycarbamoylvinyl)benzyl]benzamide; or a pharmaceutically acceptable salt thereof.

2. A pharmaceutical composition comprising a compound according to claim 1 in combination with a pharmaceutically acceptable excipient or diluent.

3. A method of treating breast cancer, lung cancer, or stomach cancer comprising administering the compound according to claim 1 to a patient.

4. A method of inhibiting histone deacetylase (HDAC) activity in at least one breast cancer, lung cancer, or stomach cancer cell comprising providing the compound according to claim 1 to said at least one breast cancer, lung cancer, or stomach cancer cell.

* * * * *